United States Patent [19]

Gharibian

[11] Patent Number: 5,527,329
[45] Date of Patent: Jun. 18, 1996

[54] SURGICAL SCALPEL

[75] Inventor: Noel Gharibian, Glendale, Calif.

[73] Assignee: Devon Industries, Inc., Chatsworth, Calif.

[21] Appl. No.: 376,065

[22] Filed: Jan. 20, 1995

Related U.S. Application Data

[63] Continuation of Ser. No. 163,938, Dec. 8, 1993, abandoned.

[51] Int. Cl.⁶ ............................................. A61B 17/32
[52] U.S. Cl. .......................... 606/167; 30/2; 30/151; 30/335; 30/162
[58] Field of Search ............................ 606/160, 167, 606/170, 172, 181, 182, 185; 30/2, 151, 162, 164, 167, 286, 335; 128/751

[56] References Cited

U.S. PATENT DOCUMENTS

| | | | |
|---|---|---|---|
| D. 327,125 | 6/1992 | Iten . | |
| D. 329,699 | 9/1992 | Schutte et al. . | |
| D. 330,082 | 10/1992 | Schutte et al. . | |
| 2,735,176 | 5/1953 | Costin . | |
| 2,885,780 | 5/1955 | Campbell | 30/162 |
| 2,968,489 | 1/1961 | Doniger | 30/162 |
| 3,025,598 | 3/1962 | Nissen . | |
| 3,657,812 | 4/1972 | Lee . | |
| 3,793,726 | 2/1974 | Schrank . | |
| 3,905,101 | 9/1975 | Shepherd . | |
| 3,906,626 | 9/1975 | Riuli . | |
| 4,091,537 | 5/1978 | Stevenson, Jr. . | |
| 4,375,218 | 3/1983 | DiGeronimo . | |
| 4,414,974 | 11/1983 | Dotson et al. . | |
| 4,491,132 | 1/1985 | Aikins | 606/167 |
| 4,523,379 | 6/1985 | Osterhout et al. . | |
| 4,660,287 | 4/1987 | Decker | 30/162 |
| 4,663,846 | 5/1987 | Takayama . | |
| 4,735,202 | 4/1988 | Williams | 606/167 |
| 4,805,304 | 2/1989 | Knoop . | |
| 4,823,457 | 4/1989 | Prochaska . | |
| 4,844,070 | 7/1989 | Dee | 606/167 |
| 4,884,569 | 12/1989 | Fedorov et al. . | |
| 4,949,458 | 8/1990 | Davis et al. . | |
| 5,055,106 | 10/1991 | Lundgrew | 606/167 |
| 5,071,418 | 12/1991 | Rosenbaum . | |
| 5,071,426 | 12/1991 | Dolgin et al. . | |
| 5,141,517 | 8/1992 | Shutt . | |
| 5,201,748 | 4/1993 | Newman et al. . | |
| 5,207,696 | 5/1993 | Matwijcow | 606/167 |
| 5,250,063 | 10/1993 | Abidin et al. | 606/167 |
| 5,250,064 | 10/1993 | Schneider . | |
| 5,299,357 | 4/1994 | Wonderley et al. . | |
| 5,309,641 | 5/1994 | Wonderley et al. . | |
| 5,312,429 | 5/1994 | Noack . | |

FOREIGN PATENT DOCUMENTS 3722899  1/1989  Germany .

*Primary Examiner*—Stephen C. Pellegrino
*Assistant Examiner*—William W. Lewis
*Attorney, Agent, or Firm*—Lyon & Lyon

[57] ABSTRACT

A surgical scalpel has a retractable sleeve. An elongated handle with a contoured grip portion is releasably attached to a blade holder securing a surgical blade. The blade holder is secured to the handle by a hook and groove assembly and a male to female connection. The sleeve slides between an extended position and a retracted position on the handle and blade holder. The extended position of the sleeve covers the blade thereby protecting operating room personnel. An arch on the sleeve contacts the hook and disengages the hook out of the groove to facilitate removal of the blade holder.

27 Claims, 7 Drawing Sheets

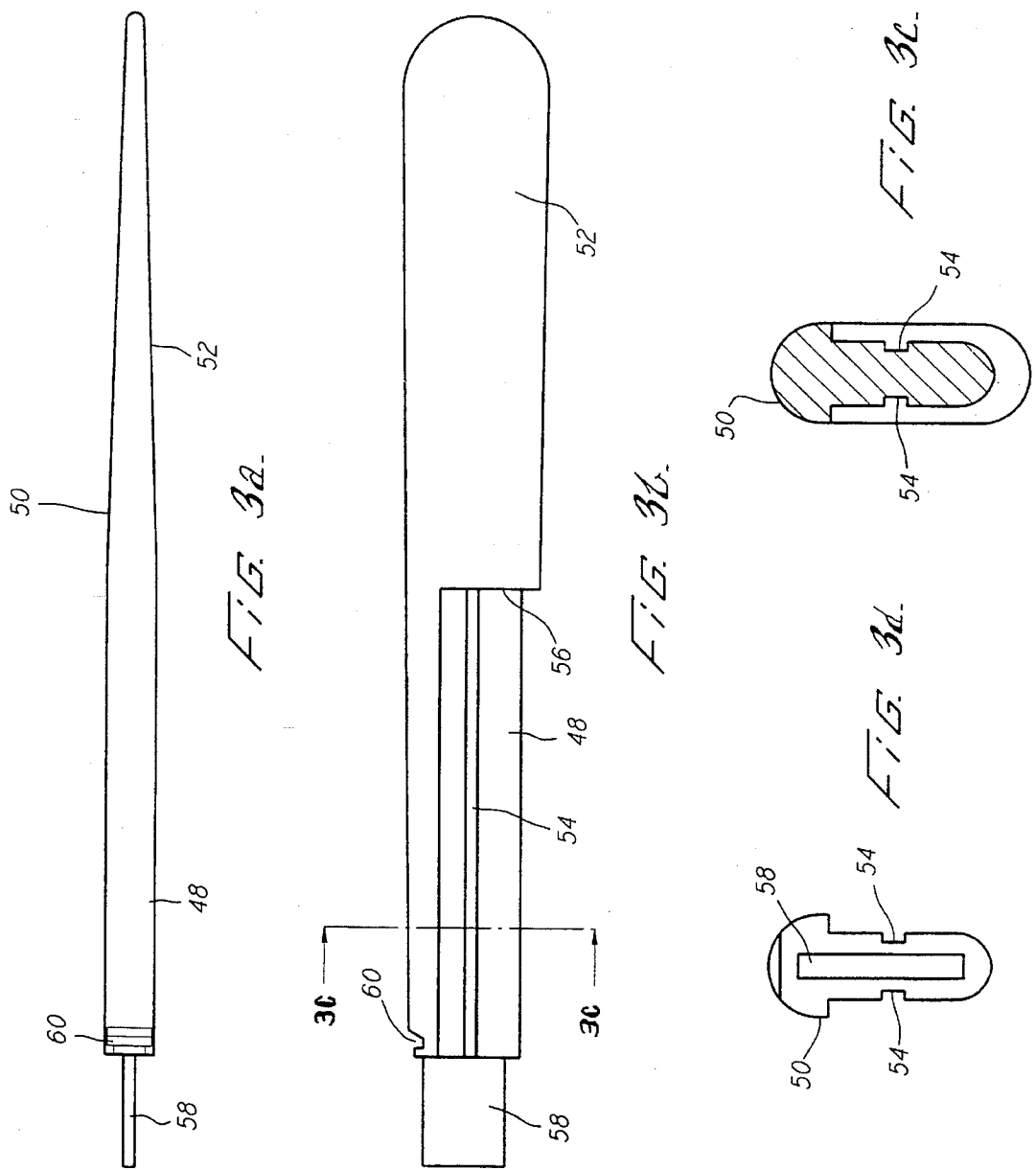

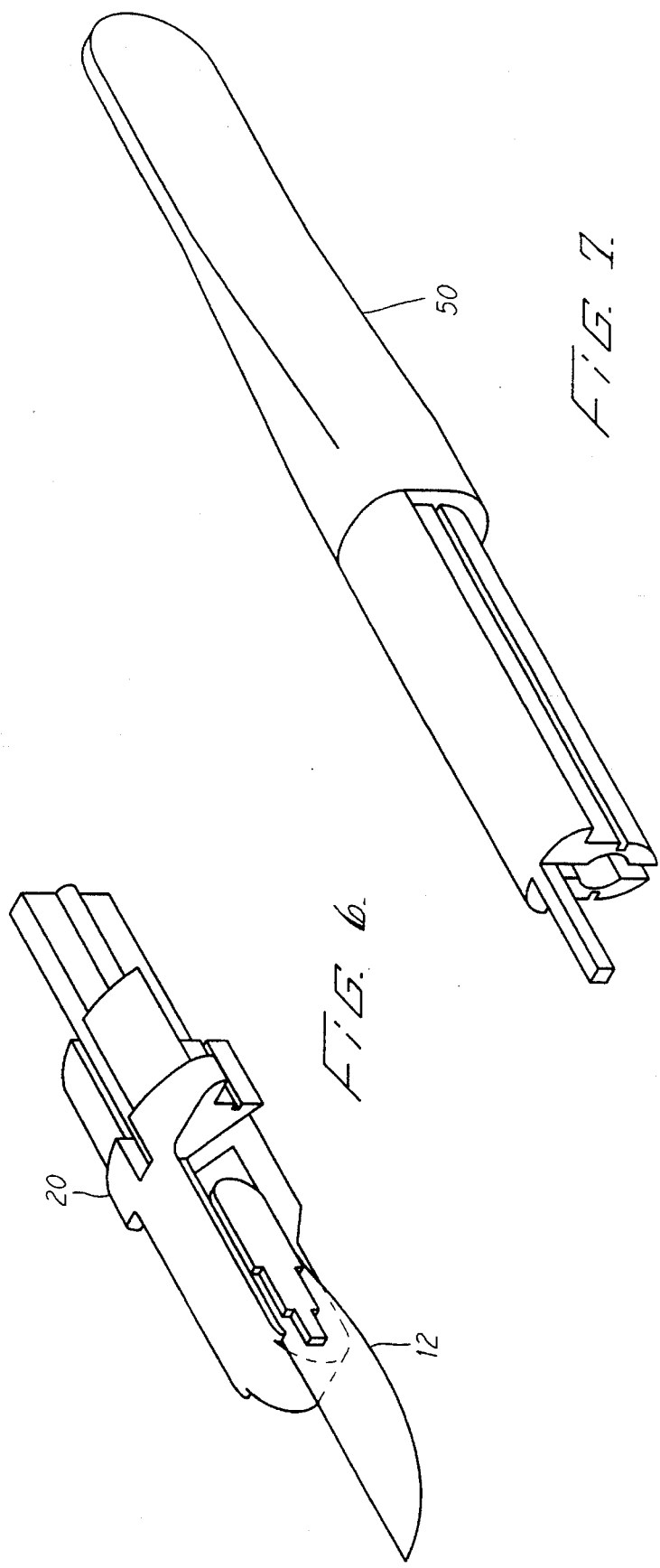

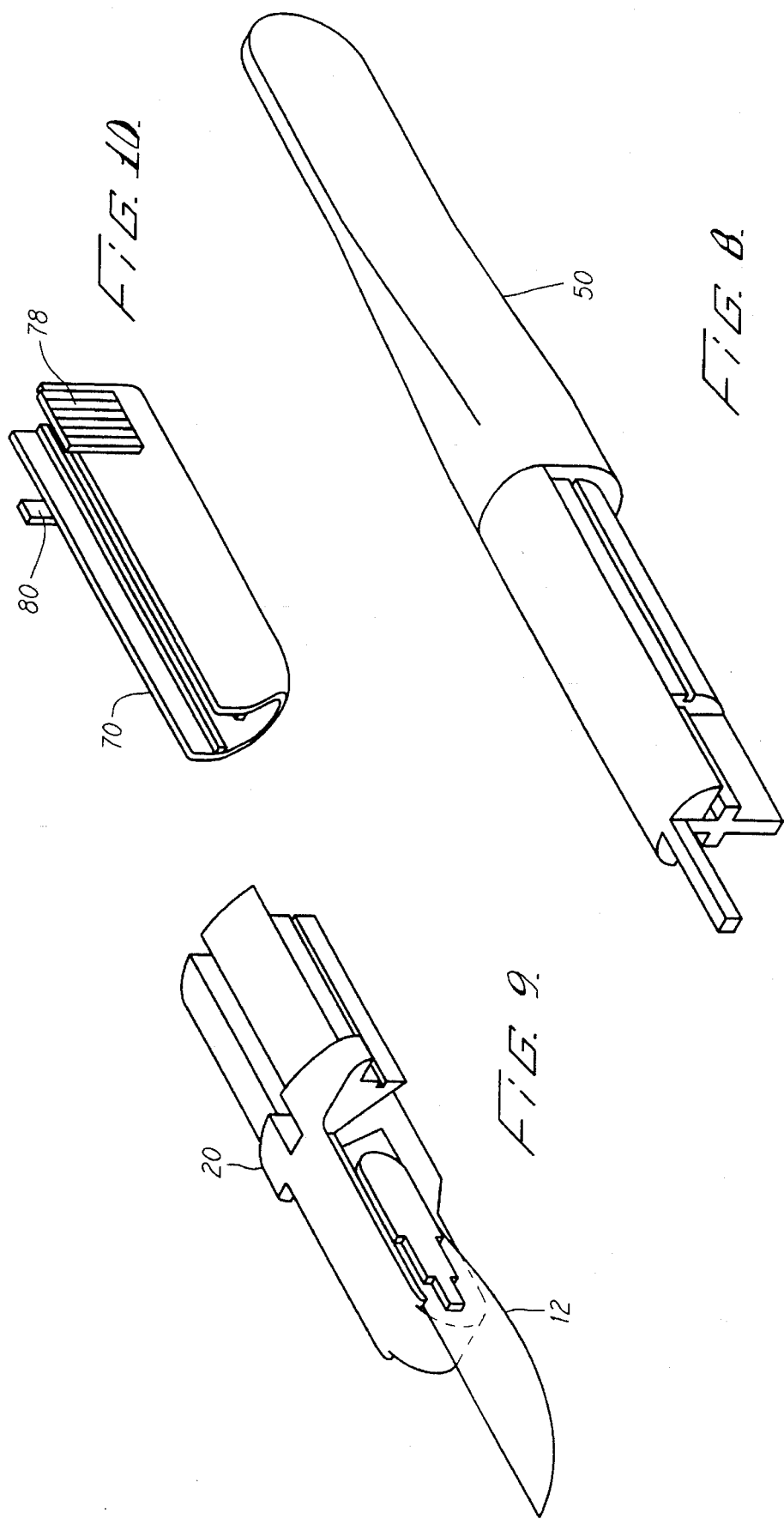

SURGICAL SCALPEL

This application is a Continuation Application of application Ser. No. 08/163,938, filed on Dec. 8, 1993, now abandoned.

BACKGROUND OF THE INVENTION

The field of the invention is surgical cutting instruments. Conventional surgical instruments provide a significant potential for harm to surgeons, nurses and other support personnel. In the operating room, various surgical instruments are quickly passed by hand. The rapid handling of such instruments with exposed sharp edges can lead to accidental cuts or puncture wounds. Surgical gloves may also be inadvertently punctured leading to loss of glove integrity further increasing the risk of infection to a surgeon, nurse or other medical personnel.

Previous attempts to guard against inadvertent cuts or punctures led to the development of retractable blade guards. Some of the earliest versions were simply retractable bladed knives used in various industries outside the medical field. These blade guards generally required two hands to operate, i.e., one hand to manipulate the blade and a second hand to secure the blade guard by turning a threaded screw. Other conventional devices having spring loaded moving parts or tabs that clipped into notches on a hollow tubed sheathing device, were not practical for surgical use because they did not provide a good grip or "feel" for the blade.

SUMMARY OF THE INVENTION

The present invention is directed to an improved scalpel. Preferably, a handle has a male or female end on one end to which a blade holder is attached. A sleeve or cover most desirably slides onto both the handle and the blade holder, preferably by guide flanges that engage channels on both pieces. The surgical blade may be exposed for use by retracting the sleeve. The blade may be covered by manually manipulating the sleeve into an extended position. In a preferred embodiment, the handle is metal and the blade holder is plastic, allowing the natural friction forces to hold them together.

The blade holder and the sleeve may advantageously be removed as a unit and the used blade easily disposed of while covered. The scalpel provides a good feel for or grip on the blade because the blade is secured to the handle. Accordingly, it is an object of the invention to provide an improved scalpel having a blade cover or sheath. Other and further objects and advantages will appear hereinafter to those skilled in the art from the following description and the accompanying drawings.

BRIEF DESCRIPTION OF THE DRAWINGS

In the drawings, wherein similar reference numbers denote similar elements throughout the several views:

FIG. 3a is a top view of the handle shown in FIG. 1;

FIG. 3b is a side elevation view of the handle illustrating the groove and a male end attachment flange;

FIG. 3c is a section view taken along line 3c—3c of FIG. 3b;

FIG. 3d is a front end view of the handle;

FIG. 6 shows a perspective view of an alternative embodiment of the blade holder with the blade attached;

FIG. 7 is a perspective view of an alternative embodiment of the handle;

FIG. 8 is a perspective view of a second alternative embodiment of the handle;

FIG. 9 is a perspective view of an alternative embodiment of the blade holder having a female end connection; and FIG. 10 is a perspective view of an alternate embodiment of the sleeve.

DETAILED DESCRIPTION OF THE PREFERRED EMBODIMENT

Figure 1:
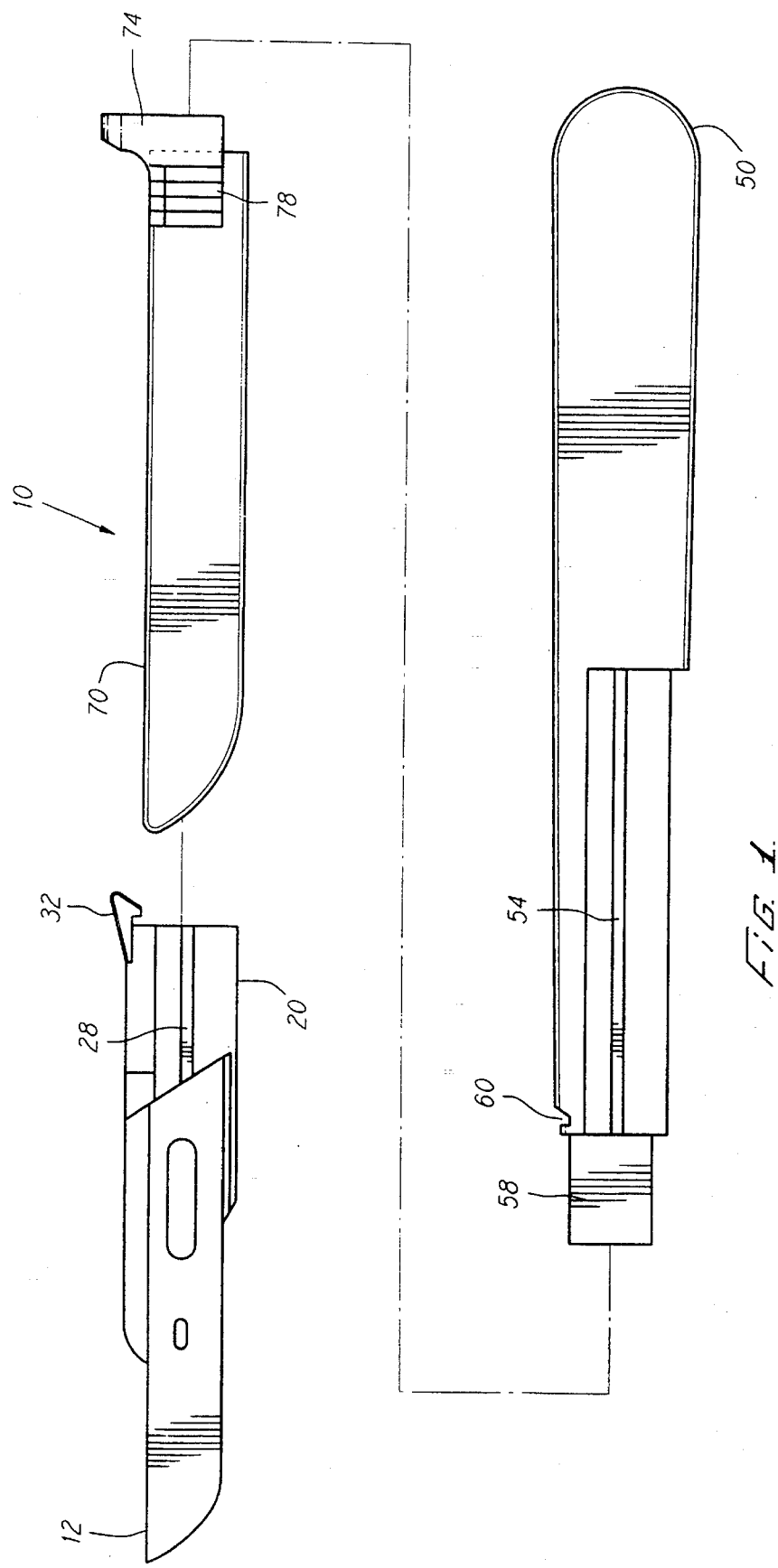
FIG. 1 is an exploded side elevation view of a preferred embodiment of the present scalpel.
Figure 2A:
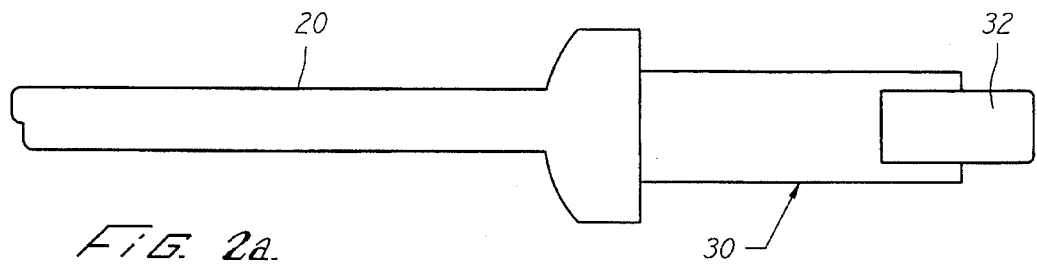
FIG. 2a is a top view of the blade holder.
Figure 2B:
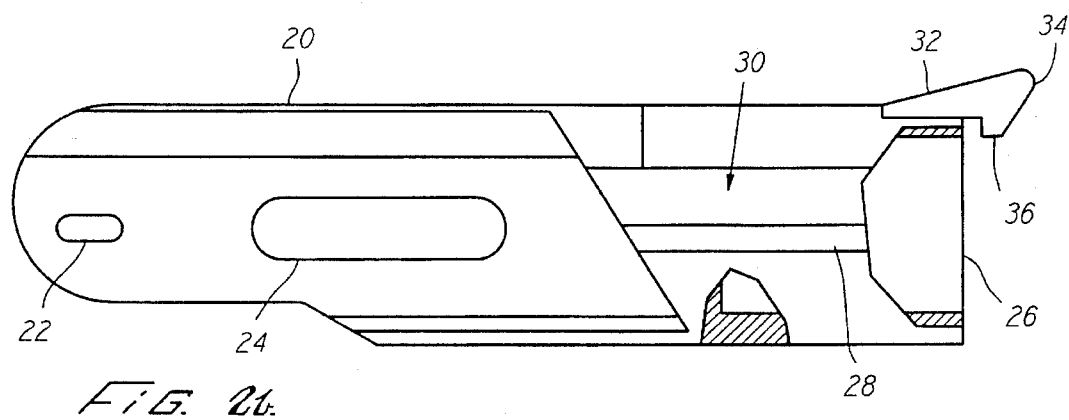
FIG. 2b is a side elevation view of the blade holder illustrating the position of the hook in the preferred embodiment and illustrating a partial section view of the attachment slot.
Figure 2C:
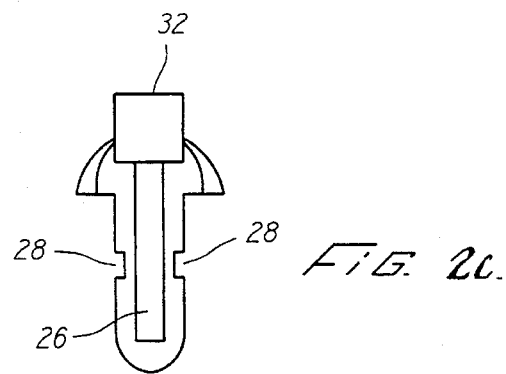
FIG. 2c is a back end view of the blade holder showing the hook and the attachment slot.
Figure 2D:
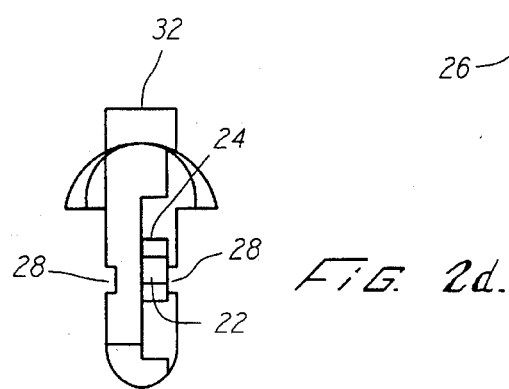
FIG. 2d is a front end view thereof.
Figure 4A:
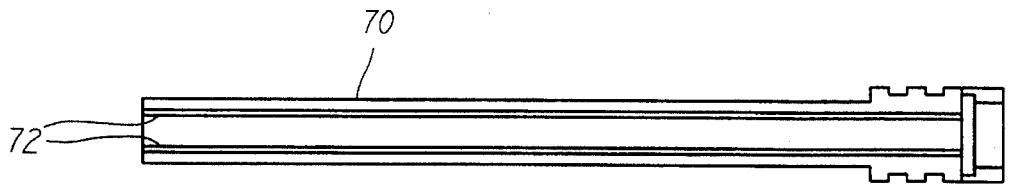
FIG. 4a is a top view of the sleeve.
Figure 4B:
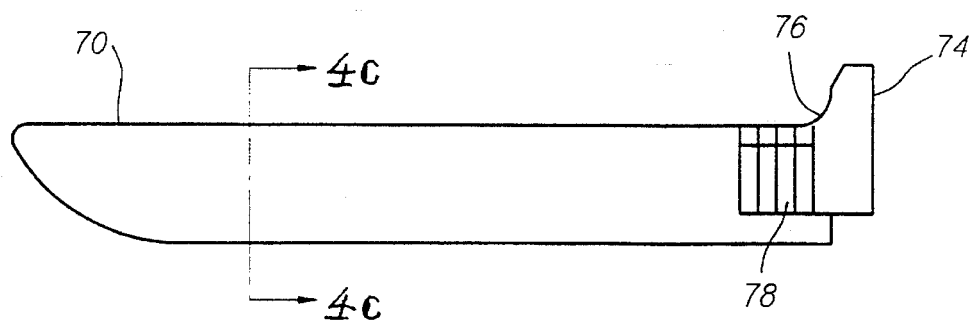
FIG. 4b is a side elevation view thereof.
Figure 4C:
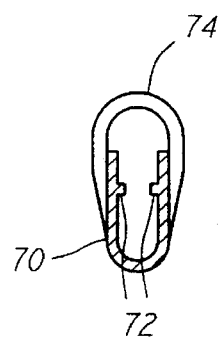
FIG. 4c is a section view of the sleeve taken along line 4c—4c of FIG. 4b.
Figure 4D:
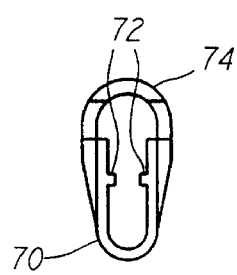
FIG. 4d is a front end view of the sleeve showing the arch.

Turning in detail to the figures, the surgical scalpel 10 is first shown in FIG. 1 with the blade 12 secured to the blade holder 20. The scalpel 10 is gripped by the handle 50 which has a preferably contoured elongated grip portion 52. As shown in FIGS. 2a and 2b, adjacent the front end of the blade holder 20 are two tabs 22 and 24 for securing the blade 12 to the blade holder 20 by interlocking with respective openings on the blade 12. Adjacent the back end of the blade holder 20 is the attachment slot 26 shown as a female end connection. Channels 28 are positioned longitudinally on opposite sides of the blade holder 20 along a channel section 30 of the blade holder 20.

A hook 32 is cantilevered from the back end of the blade holder 20. The hook 32 can resiliently flex upwardly and downwardly to engage the handle 50. The cantilevered end of the hook 32 has an inclined aft surface 34 and a protrusion 36 which is adapted to engage a complementary shaped groove 60 on the handle 50 when the blade holder 20 mates with the handle 50.

Referring now to FIGS. 3a and 3b, a pair of guide channels 54 are provided on opposite sides of the guide channel section 48 of the handle 50 in front of the grip portion 52. The guide channels 54 terminate at detents 56 where the guide channel section 48 adjoins the grip portion 52.

An attachment flange 58 (shown as a male ended attachment) is joined to the front end of the guide channel section 48. As shown in FIGS. 3b and 3d, the attachment flange 58 is generally rectangular in cross section, although other configurations are possible, and is adapted to mate with the attachment slot 26 of the blade holder 20. A groove 60 at the forward end of the guide channel section 48 is shaped to mate with the hook 32.

Next referring to FIGS. 4a through 4d, the sleeve 70 is generally U-shaped in cross section having a closed bottom portion and an open upper portion. A pair of guide flanges 72 are positioned within the sleeve 70 and are adapted to engage the guide channels 54 and 28. An arch 74 at the back end of the sleeve 70 spans between the two sides of the sleeve 70. The arch 74 preferably has a radiused front surface 76.

Figure 5A:
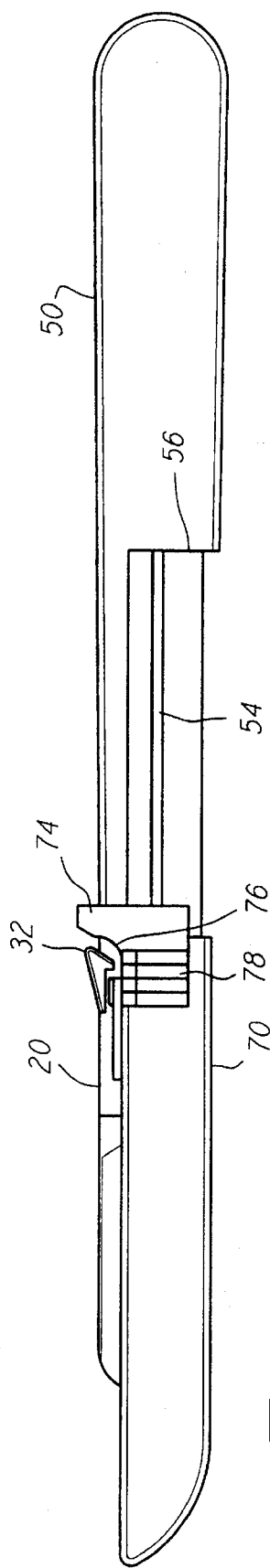
FIG. 5a is a side elevation view of the assembled scalpel with the sleeve positioned in an extended position.

The sleeve 70 preferably has a digit engaging portion 78 adjacent to the arch 74 having a series of ribs forming a thumb rest. The digit engaging portion 78 improves the surgeon's "feel" for the sleeve 70 when the sleeve 70 slides along the guide channels 28 and 54 by hand or thumb pressure. FIG. 5a shows an assembled scalpel 10 with the sleeve 70 in a forward position to cover or sheath the blade 12. The forward movement of the sleeve 70 is guided by the guide flanges 72 that travel along the guide channels 28 and 54. With the sleeve 70 moved fully forward, the radiused surface 76 contacts the hook 32 to stop additional forward movement. Additional forward movement by the sleeve 70 toward the extended position as guided by the user's hand will cause the arch 74 to lift the hook 32 out of the groove 60 for removal of the blade holder 20 from the handle 50. This allows the sleeve 70 and blade holder 20 to be disassembled as a unit from the handle 50 while the blade 12 is sheathed by the sleeve 70, thus minimizing the risks of inadvertent cuts. The blade 12, blade holder 20 and sleeve 70 may then be disposed of. The handle may advantageously be reused.

Figure 5B:
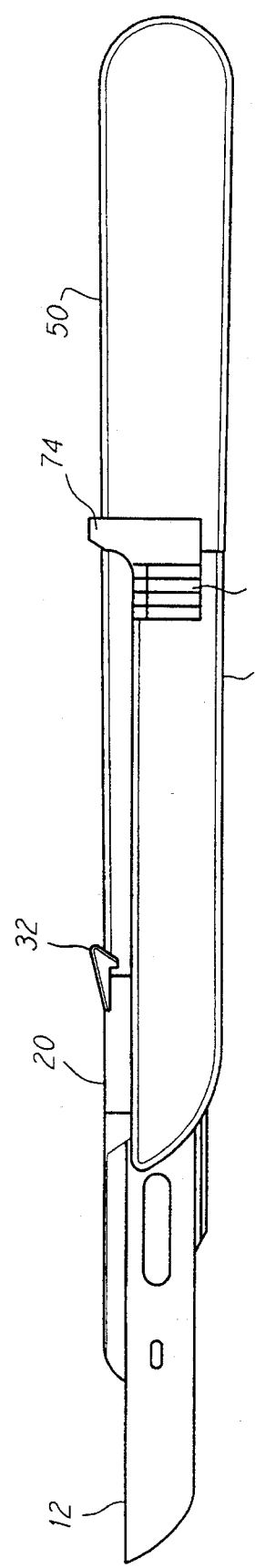
FIG. 5b is an elevation view thereof with the sleeve in a retracted position.
Figure 5C:
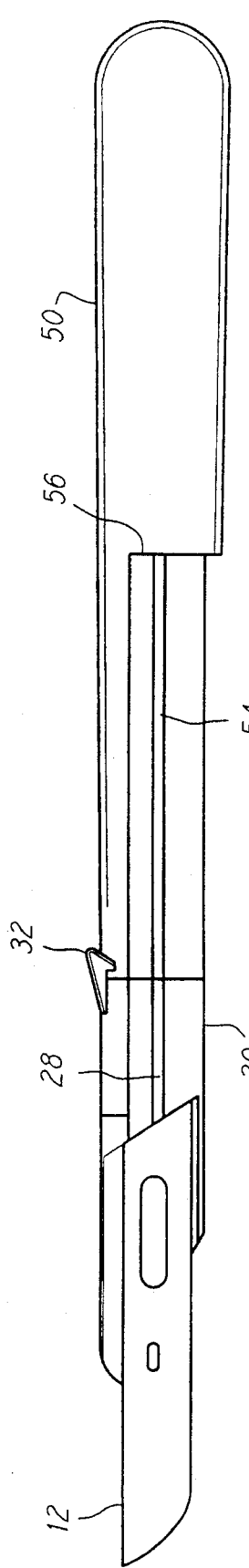
FIG. 5c is a side elevation view with the sleeve removed.

FIG. 5b shows the sleeve 70 moved to the fully retracted position with the back end of the sleeve 70 abutting the detents 56 to fully expose the blade 12. The user may utilize the digit engaging portion 78 on the sleeve 20 to improve fingertip control of the longitudinal front to back movement of the sleeve 70. FIG. 5c shows the sleeve 70 removed from the handle 50 (for purposes of illustration).

FIG. 6 illustrates an embodiment of the blade holder 20 with both a male ended attachment and a female ended slot. FIG. 7 shows an embodiment of the handle 50 which mates with the blade holder 20 shown in FIG. 6. An alternative embodiment of the handle 50 is also shown in FIG. 8 with male ended connections. An embodiment of the blade holder 20 which mates with the handle 50 of FIG. 8 is further shown in FIG. 9 with an outline of the attached blade 12. An alternative embodiment of the sleeve 70 is shown in FIG. 10 which illustrates a stop tab 80 which may be utilized to stop forward longitudinal sliding of the sleeve 70. An inclined digit engaging portion 78 feature is illustrated and may be used to facilitate use as a thumb rest for the operating surgeon.

While a preferred embodiment of the present invention has been shown and disclosed in the drawings and specification, alternate embodiments of the present invention would be apparent to the person of ordinary skill in the art and this application is intended to include those embodiments within the full breadth and scope of the claims. Moreover, the present invention need not include all of the features disclosed in the single embodiment but rather one or more features may be included.

What is claimed is:

1. A surgical instrument for holding a cutting blade comprising:

a blade holder having a guide channel;

a handle having a groove and guide channels;

attachment means for attaching the blade holder to the handle;

a hook resiliently attached to said blade holder and engageable with said groove; and a sleeve having guide flanges engaging said guide channels of said handle and said holder, with said sleeve slidable in a longitudinal direction along said blade holder and said handle between an extended position and a retracted position.

2. The instrument of claim 1 where said blade holder is a plastic material and said handle is a metallic material.

3. The instrument of claim 1 further comprising a cutting blade attached to said blade holder.

4. The instrument of claim 1 further comprising detents on said handle to limit movement of said sleeve by said sleeve engaging said detents.

5. The instrument of claim 1 where said handle is releasably secured to said blade holder by a male ended member disposed on the handle which releasably interconnects to a female ended slot disposed on the blade holder.

6. The scalpel of claim 1 where said handle is releasably secured to said blade holder by a male ended member disposed on the blade holder which releasably interconnects to a female ended slot disposed on the handle.

7. A surgical scalpel comprising:

a surgical cutting blade;

a blade holder comprising guide channels;

means for releasably securing said blade holder to said cutting blade at a front end of said blade holder;

a handle comprising a groove and guide channels;

holding means for holding said blade holder and said handle together, said holding means attached to said blade holder and adapted to engage said groove; and a sleeve comprising an arch and guide flanges adapted to engage said guide channels for controlled longitudinal sliding movement of said sleeve on said blade holder and said handle between an extended position and a retracted position, said arch adapted to contact said holding means and lift said holding means away from said groove by sliding movement of said sleeve toward said extended position.

8. The scalpel of claim 7 where said blade holder is a plastic material and said handle is a metallic material.

9. The scalpel of claim 7 where said handle comprises detents to limit retraction of said sleeve by said sleeve engaging said detents.

10. The scalpel of claim 7 where said handle is releasably secured to said blade holder by a male ended member disposed on the handle which releasably interconnects with a female ended slot disposed on the blade.

11. The scalpel of claim 7 where said handle is releasably secured to said blade holder by a male ended member disposed on the blade holder which releasably interconnects with a female ended slot disposed on the handle.

12. A surgical instrument comprising:

a handle having a groove;

a blade holder releasably attached to said handle by a male ended member disposed on the handle which connects with a female ended slot disposed on the blade holder, said blade holder having a hook adapted to releasably mate with said groove;

a sleeve having an arch and adapted to be slidably positioned by controlled longitudinal movement in communication with said handle and said blade holder between an extended position and a retracted position, said arch adapted to lift said hook away from said groove by moving between said hook and groove with said controlled longitudinal movement of said sleeve toward said extended position to facilitate removal of said blade holder from said handle.

13. The instrument of claim 12 further comprising a surgical cutting blade releasably secured to said blade holder.

14. The instrument of claim 12 where said sleeve further comprises a digit engaging portion.

15. The instrument of claim 12 where said handle further comprises a tapered grip portion.

16. The instrument of claim 12 where said hook further comprises an inclined aft surface and a protrusion.

17. The instrument of claim 12 where said blade holder is plastic and said handle is metal.

18. The instrument of claim 12 where said arch comprises a radiused front surface.

19. The instrument of claim 12 where said sleeve comprises a stop tab.

20. A surgical instrument comprising:

a handle;

a blade holder;

means for locking said blade holder onto the handle;

a blade cover slidably attached to the handle; and means for unlocking the blade holder from the handle in response to movement of the blade cover over the blade holder past a predetermined point on the blade holder.

21. An assembly for holding a surgical scalpel blade onto a handle comprising:

a blade holder including:
 a front section having a tab fitting for mounting the scalpel blade;
 a rear section having a pair of longitudinal channels on opposite sides of the rear section; and
a sleeve including:
 a back end having an arch adapted to engage the hook and move it in a second direction opposite to the first direction; and
 a pair of guide flanges adapted to slidably engage the longitudinal channels on the blade holder.

22. The assembly of claim 21 wherein the blade is attached to the blade holder via the tab fitting.

23. The assembly of claim 21 further comprising a digit engaging portion on the sleeve.

24. The scalpel of claim 23 further comprising a cutting blade attached to said blade holder.

25. The assembly of claim 21 wherein the sleeve is U-shaped.

26. A blade holder and sheath combination for use with a surgical scalpel handle comprising:

a blade holder having first attachment means to releasably secure said blade holder to the scalpel handle and including holding means to hold said blade holder and the scalpel handle together;

a sheath slidably adjoining the scalpel handle and said blade holder for controlled longitudinal sliding movement of said sheath along said blade holder and the scalpel handle for exposing or covering a blade; and disengaging means on said sheath for disengaging the holding means.

27. A surgical scalpel comprising:

a handle having a groove;

a blade holder releasably attached to said handle by a male ended member disposed on the blade holder which connects with a female ended slot disposed on the handle, said blade holder having a hook adapted to releasably mate with said groove;

a sleeve having an arch and adapted to be slidably positioned by controlled longitudinal movement in communication with said handle and said blade holder between an extended position and a retracted position, said arch adapted to lift said hook away from said groove by moving between said hook and groove with said controlled longitudinal movement of said sleeve toward said extended position to facilitate removal of said blade holder from said handle.

* * * * *